(12) United States Patent
Benner

(10) Patent No.: US 10,513,704 B2
(45) Date of Patent: Dec. 24, 2019

(54) BINDING AND CATALYTIC MOLECULES BUILT FROM L-DNA WITH ADDED NUCLEOTIDES

(71) Applicant: Steven A Benner, Gainesville, FL (US)

(72) Inventor: Steven A Benner, Gainesville, FL (US)

(*) Notice: Subject to any disclaimer, the term of this patent is extended or adjusted under 35 U.S.C. 154(b) by 2 days.

(21) Appl. No.: 15/639,336

(22) Filed: Jun. 30, 2017

(65) Prior Publication Data

US 2017/0298356 A1  Oct. 19, 2017

Related U.S. Application Data

(63) Continuation-in-part of application No. 14/082,800, filed on Nov. 18, 2013, now Pat. No. 9,725,713, which is a continuation-in-part of application No. 13/493,172, filed on Jun. 11, 2012, now Pat. No. 8,586,303, which is a continuation-in-part of application No. 12/999,138, filed on Dec. 15, 2010, now Pat. No. 8,614,072.

(51) Int. Cl.
*C12N 15/115* (2010.01)
*C12P 19/34* (2006.01)
*C12Q 1/6811* (2018.01)

(52) U.S. Cl.
CPC ............ *C12N 15/115* (2013.01); *C12P 19/34* (2013.01); *C12Q 1/6811* (2013.01); *C12N 2310/16* (2013.01); *C12N 2310/33* (2013.01)

(58) Field of Classification Search
CPC .................................................... C12N 15/115
USPC ........................................................... 435/6.1
See application file for complete search history.

(56) References Cited

PUBLICATIONS

Sismour et al. "The use of thymidine analogs to improve the replication of an extra DNA base pair: a synthetic biological system" Nucleic Acids Research, vol. 33, No. 17, pp. 5640-5646. (Year: 2005).*

* cited by examiner

*Primary Examiner* — Jezia Riley

(57) ABSTRACT

This invention provides for processes for binding to and/or chemically transforming a preselected target, where the process involves contacting said target to an oligonucleotide molecule that contains one or more "non-standard" nucleotides, which are nucleotide analogs that, when incorporated into oligonucleotides (DNA or RNA, collectively xNA), present to a pattern of hydrogen bonds that is different from the pattern presented by adenine, guanine, cytosine, and uracil. This disclosure provides an example where such an oligonucleotide molecule is built from both D- and L-mirror image carbohydrates in the backbone. It also provides a process for obtaining these binders and/or transformers by a laboratory in vitro selection process that exploits rolling circle amplification rather than the polymerase chain reaction.

14 Claims, 6 Drawing Sheets

BINDING AND CATALYTIC MOLECULES BUILT FROM L-DNA WITH ADDED NUCLEOTIDES

CROSS REFERENCE TO RELATED APPLICATIONS

This application is a continuation-in-part of the currently pending U.S. patent application Ser. No. 14/082,800, filed 18 Nov. 2013 for "In vitro selection with expanded genetic alphabets", which is a continuation-in-part of the U.S. patent application Ser. No. 13/493,172, filed on Jun. 11, 2012 for In vitro selection with expanded genetic alphabets", now U.S. Pat. No. 8,586,303, which is a continuation-in-part of the U.S. patent application Ser. No. 12/999,138, filed Dec. 15, 2010 for "Polymerase incorporation of non-standard nucleotides", now U.S. Pat. No. 8,614,072. It claims the benefit of these parents.

STATEMENT OF RIGHTS TO INVENTIONS MADE UNDER FEDERALLY-SPONSORED RESEARCH

None

NAMES OF THE PARTIES TO A JOINT RESEARCH AGREEMENT

Not applicable.

INCORPORATION-BY-REFERENCE OF MATERIAL SUBMITTED ON A DISC

None.

BACKGROUND OF THE INVENTION (1) Field of invention

This invention relates to the field of nucleic acid chemistry, more specifically to nucleotide analogs, and still more specifically to "non-standard" nucleotide building blocks that, when incorporated into oligonucleotides (DNA or RNA, collectively xNA), present to a complementary strand in a Watson-Crick pairing geometry a pattern of hydrogen bonds that is different from the pattern presented by adenine, guanine, cytosine, and uracil. Further, this invention relates to nucleic acid analogs that fold in a way that allows them to bind to target molecules by mechanisms other than Watson-Crick hybridization (aptamers), and nucleic acid analogs that chemically transform the molecules that they bind (aptazymes). These are such molecules are often called "aptamers" are "aptazymes"). Most specifically, this invention claims process that involving the binding and/or catalysis by nucleic acid analogs that contain non-standard building blocks where the oligonucleotide themselves is built from building blocks having either the D- or L-absolute configuration.

(2) Description of Related Art

For two decades, many have sought processes that mimic, in the laboratory, biological evolution to select or evolve DNA or RNA (collectively xNA) molecules that act as ligands, receptors, or catalysts. This process has been called Systematic Evolution of Ligands by Exponential Enrichment (SELEX), "in vitro selection", in vitro evolution, or "laboratory in vitro evolution (LIVE). These process are collectively referred to here as LIVE. The xNA ligands and receptors that bind to a preselected target are often called aptamers. xNA molecules that catalyze a preselected reaction are often called aptazymes.

The literature describing the history of development of LIVE is summarized in the U.S. patent applications Ser. Nos. 13/493,172 and 14/082,800, which rely on technology disclosed in the U.S. patent application Ser. No. 12/999,138. All of these patent applications (collectively called the "parents") are incorporated in their entireties by reference, including their drawings, abstract, and disclosures, including examples.

As generally'practiced, LIVE generates aptamers or aptazymes by the following steps:

(a) A library of nucleic acid (xNA) molecules (typically $10^{14}$ to $10^{14}$ different species) is obtained.

(b) The library is then fractionated to create a fraction that contains molecules better able bind to the preselected target(s), or catalyze the preselected reaction(s), than molecules in the fractions left behind. For example, to generate aptamers, this separation can be done by contacting the library with a solid support carrying the target, washing from the support xNA molecules that do not bind, and recovering from the support xNA molecules that have bound. xNA molecules within the library that bind to the target are said to survive the selection.

(c) The surviving xNAs are then used as templates for the polymerase chain reaction (PCR) process. A low level of mutation may be included in the PCR amplification, creating Darwinian "variation" in an in vitro evolution process.

(d) While aptamers/aptazymes having useful binding/catalytic activity may emerge in the first "round" of selection, they generally do not. When they do not, the cycle is repeated. With each cycle of fractionation/selection and PCR amplification, the resulting fraction of xNA molecules becomes more enriched in those that bind to the preselected target or catalyze the preselected reaction.

(e) The product xNA aptamer(s) and aptazyme(s) might be useful if their sequences are not known. However, the utility'of these products is often enhanced if their sequences are known, as this allows them to be generated separately. To obtain those sequences, standard LIVE procedures generally clone the xNA products in their DNA form (either directly for DNA products, or after conversion to a DNA sequence using reverse transcriptase for RNA products) followed by classical sequencing. Alternatively, next generation sequence can be applied to the mixture of survivors. The elements of this approach are reviewed in U.S. Ser. Nos. 13/493,172 and 14/082,800.

U.S. Ser. Nos. 13/493,172 and 14/082,800 also review the many attempts to improve. LIVE with functionalized natural DNA and RNA. However, simply functionalizing standard xNA nucleotides (as in SOMAmers) does not greatly expand its diversity of folds. Nor does it increase the information density of the biopolymer. Further, functionalizing GACT encounters a new set of problems. For example, an xNA molecule having a fluorescent group attached to each nucleobase are hard to make using xNA polymerases. Further, in ways that are not fully understood, having each nucleobase carry a functional group can cause the DNA to cease to follow "rule based" molecular recognition essential for its genetic roles.

U.S. Ser. No. 13/493,172 also discussed how many of the disadvantages of standard LIVE aptamers and aptazymes might be mitigated by expanding the number of nucleotides in DNA. For example, rearranging hydrogen bond donor and acceptor groups on the nucleobases increases the number of independently replicable nucleosides in DNA and RNA from four to twelve (FIG. 1 and FIG. 2). In this "artificially expanded genetic information system" (AEGIS), as many as 12 different nucleotide "letters" pair via as many as six distinguishable hydrogen bonding patterns to give a system that can be copied and evolve like natural DNA, using processes disclosed in the parents. The products are oligonucleotides with higher information density and more functional group diversity than standard DNA or RNA (collectively xNA).

The potential for using AEGIS to support LIVE has been recognized since the proposal of the first AEGIS. Indeed, processes for doing LIVE with certain AEGIS-containing nucleotides were offered by U.S. Pat. No. 5,965,363. However, efforts to implement the process disclosed in that patent failed to work experimentally. Steps (a) and (b) (above) in the LIVE process were possible. Libraries of xNA molecules containing AEGIS components could be prepared, Step (a), and these libraries could be fractionated (Step (b)). However, as discussed in U.S. Ser. No. 13/493,172, polymerases were not available to perform PCR on DNA molecules containing multiple AEGIS nucleotides.

BRIEF SUMMARY OF THE INVENTION

The parents cover and claim processes for creating aptamers and aptazymes that incorporate AEGIS. Two issues are addressed in the instant application to further increase the utility of these products. The first recognizes that the more AEGIS components one has in such products, the better they generally perform. Even with the improved polymerases described in the parents, AEGIS components are often lost in the PCR amplification process that occurs in standard LIVE in between selection steps. This is because in PCR, a majority of the products come from copying the copies of the copies, and so on. In each copying step, an opportunity exists for information to be lost, just as repeated Xerox copying of a Xerox of a copy of a Xerox copy will lead to low information. This application discloses anew approach to LIVE that uses rolling circle amplification rather than PCR to amplify survivors of a selection step. The second advance reported in the instant application relates to the desire to use AEGIS aptamers and aptazymes in complex biological media that contain enzymes that bind and digest xNA. These enzymes are known, however, to act only on xNA molecules that are built from nucleosides where the ribose or 2'-deoxyribose has a "D-configuration"; this corresponds to a 4'-R absolute configuration. However, the AEGIS-containing aptamers and aptazymes are not digested by nucleases where the ribose or 2'-deoxyribose has the mirror image "L-configuration"; this corresponds to a 4'-S absolute configuration. This is well known in fully standard xNA molecules that do not contain AEGIS components [Eulberg, D., Klussmann, S. (2003). Spiegelmers. Biostable aptamers. *Chembiochem* 4, 979-983]. However, hitherto, no oligonucleotides containing AEGIS built from L-nucleosides have'been reported. This invention provides xNA analogs containing both AEGIS components and L-nucleosides.

Most specifically in its presently preferred embodiments, this invention concerns the use, as aptamers and aptazymes, of AEGIS-containing oligonucleotide analogs where the AEGIS components are, without limitation:

2-amino-8-(1'-β-D-2'-deoxyribofuranosyl)-imidazo[1,2-a]-1,3,5-triazin-4(8H)one (trivially called D-dP where the initial "D" indicates the stereochemical configuration of the ribose, and "d" indicates that the species is the 2'-deoxynucleoside), 2-amino-8-(1'-β-L-2'-deoxyribofuranosyl)-imidazo[1,2-a]-1,3,5-triazin-4(8H)one (trivially called L-dP where the initial "L" indicates the stereochemical configuration of the ribose, and "d" indicates that the species is the 2'-deoxynucleoside), 6-amino-5-nitro-3-(1'-β-D-2'-deoxyribofuranosyl)-2(1H)-pyridone (trivially called D-dZ), 6-amino-5-nitro-3-(1'- β-L-2'-deoxyribofuranosyl)-2(1H)-pyridone (trivially called L-dZ), 4-Amino-7- [2'-deoxy-5-beta-D-erythropentofuranosyl]1,7-dihydro-2H-pyrrolo[2,3-d]-pyrimidin-2-one (trivially called D-dB, or 7-deazaisoguanosine), and isocytosine heterocycles.

4-Amino-7-[2'-deoxy-5-beta-L-erythropentofuranosyl]1,7-dihydro-2H-pyrrolo[2,3-d]-pyrimidin-2-one (trivially called L-dB, or 7-deazaisoguanosine), and isocytosine heterocycles.

2-amino-5-methyl-1-(1'-beta-D-2'-deoxyribofuranosyl)-4(1H)-pyrimidinone, (trivially called D-dS, or isocytidine) and/or 2-amino-5-methyl-1-(1'-beta-L-2'-deoxyribofuranosyl)-4(1H)-pyrimidinone, (trivially called L-dS, or isocytidine)

DESCRIPTION OF INVENTION

Figure 1:
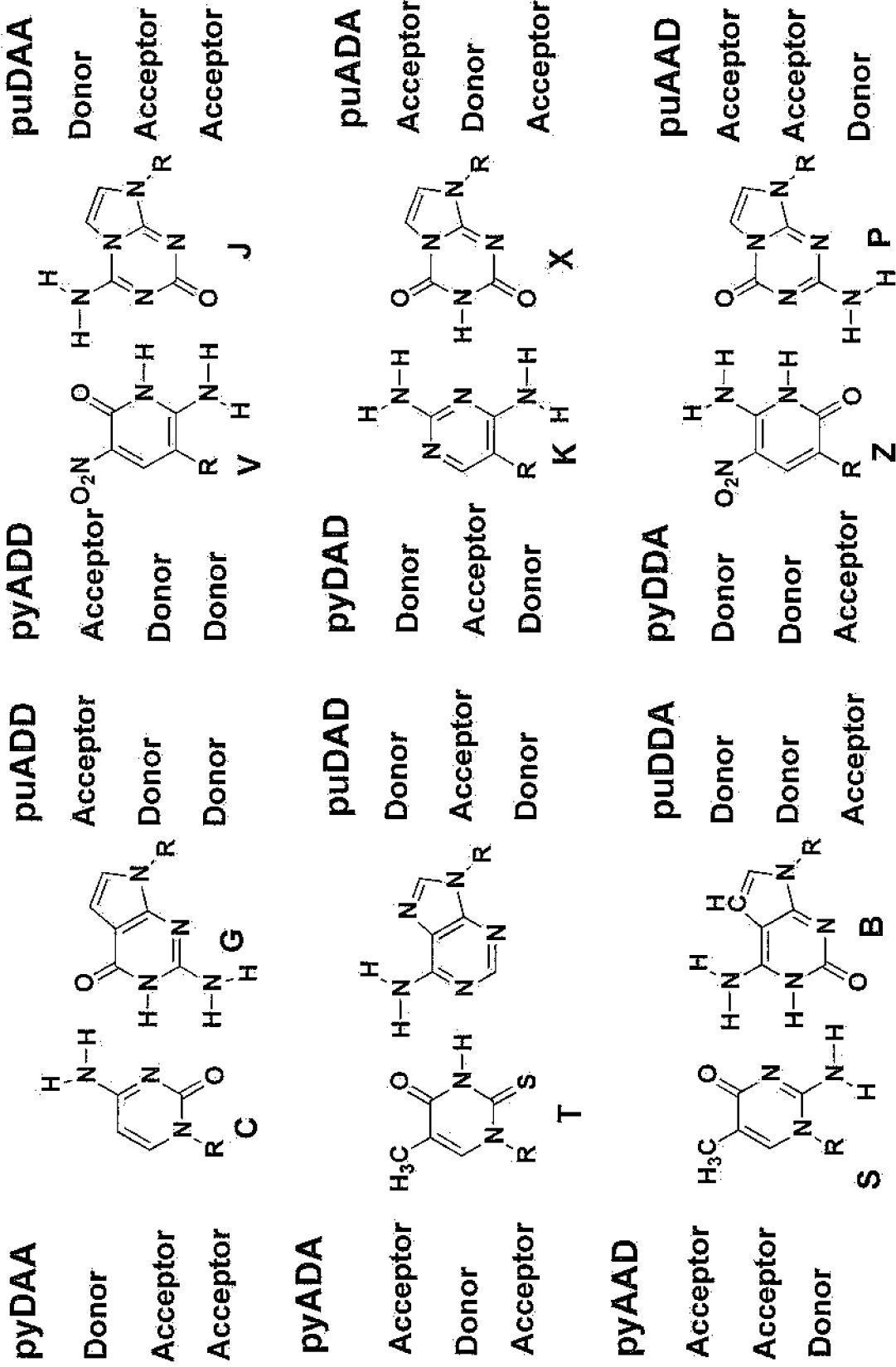
FIG. 1. Watson-Crick pairing rules follow two rules of complementarity: (a) size complementarity (large purines pair with small pyrimidines) and (b) hydrogen bonding complementarity (hydrogen bond donors, D, pair with hydrogen bond acceptors A). Rearranging D and A groups on various heterocycles supports an artificially expanded genetic information system (AEGIS). AEGIS nucleobases can also be functionalized at the position indicated by the "R" in these structures. These are the presently most preferred heterocycles for the instant invention. The nucleotides herein that are not found in natural DNA or RNA are called "non-standard".

Definition of Non-standard Components of an Artificially Expanded Genetic Information System This application teaches a distinction between the hydrogen-bonding pattern (in FIG. 1 and FIG. 2 nomenclature, pyDAD, for example) and the heterocycle that implements it. Thus, the pyADA hydrogen-bonding pattern is implemented by thymidine, uridine, and pseudouridine. The puDDA hydrogen bonding pattern is implemented by both the heterocycle isoguanosine and 7-dear-isoguanosine. Heterocycles to implement any particular pre-selected hydrogen-bonding pattern are preferred depending on their chemical properties, for example, high chemical stability or low tautomeric ambiguity. The pyADA, pyDAA, puADD, and puDAD hydrogen bonding patterns are said to be "standard" hydrogen bonding patterns, and to form with their appropriate complement "standard base pairs". Other hydrogen bonding patterns are said to be "non-standard", and to form with their appropriate complement "non-standard base pairs".

Creating AEGIS-containing Oligonucleotides Having all of the Carbohydrate Suitors in the L-configuration The strategy to generate binding and reactive AEGIS sequences that are stable in cancer-relevant biological environments relies in our ability to present them in their mirror-image form. These in AEGIS-free oligonucleotides are not be substrates for any natural nucleases, including those found in human blood and tissues; mirror image xNA is stable in blood, for example, for as long as 72 hours [Kim, K. R., Lee, T., Kim, B. S., & Ahn, D. R. (2014). Utilizing the bioorthogonal base-pairing system of L-DNA to design ideal DNA nanocarriers for enhanced delivery of nucleic acid cargos. *Chem. Sci.* 5, 1533-1537.].

Synthesis of L-AEGIS oligonucleotides is implemented using solid phase phosphoramidite chemistry, well known in the art. The only difference is that the phosphoramidite building blocks have the L configuration, and are prepared by one of the processes described in the drawings.

The sequence for the L-AEGIS oligonucleotide(s) that bind and/or chemically transform to an achiral target is obtained simply by following the processes disclosed in the parents. Since the target is not chiral, the L-AEGIS oligonucleotide will bind to and/or chemically transform that achiral target with exactly the same affinity and/or exactly the same rate as the D-AEGIS oligonucleotide.

The sequence for the L-AEGIS oligonucleotide(s) that bind and/or chemically transform to a chiral target is obtained by following the processes disclosed in the parents, except by using the target in its mirror image enantiomeric form. The processes disclosed in the parents wilt generate D-AEGIS oligonucleotide(s) that bind to and/or chemically transform that chiral target in the form that is the mirror image of the desired target, Then, by symmetry laws in physics, the L-AEGIS oligonucleotide will bind to and/or chemically transform the chiral target in the desired enantiomeric form with exactly the same affinity and/or exactly the same rate as the D-AEGIS oligonucleotide binds to and/or transforms the target in its mirror image enantiomeric form.

When the desired target is a natural translated protein, which is built from L-amino acids, the target must be the same protein sequence, except built from D-amino acids, Kent and his colleagues have used convergent synthesis to make mirror-image proteins that are arbitrarily large [Kent, S. B. (2009). Total chemical synthesis of proteins. *Chemical Society Reviews* 38, 338-351.]. His technology is an alternative should we encounter the pitfall that no loops create AEGISbodies. Alternatively, AEGIS-LIVE may be targeted against a surface loop peptide of a target protein, preferably a flexible surface loop peptide, in the target protein, but synthetic so that it is built from D-amino acids [Rowlands, D. J., Clarke, B. E., Carroll, A. R., Brown, F., Nicholson, B. H., Bittle, J. L., Houghten, R. A. & Lerner, R. A. (1983) Nature (London) 306, 694-697.] [Alexander, H., Johnson, D. A., Rosen, J., Jerabek, L., Green, N., Weissman, I. L. & Lerner, R. A. (1983) Nature (London) 306, 697-699.] [Geysen, H. M., Barteling, S. J., & Meloen, R. H. (1985). Small peptides induce antibodies with a sequence and structural requirement for binding antigen comparable to antibodies raised against the native protein. *Proc. Natl. Acad. Sci. USA* 82, 178-182.]. This presently preferred process follows rules to how to extract peptides from a full protein to serve for this purpose [Walter, G. (1986). Production and use of antibodies against synthetic peptides, *J. Immunol. Meth.* 88, 149-161.

To force the peptide to adopt a turn conformation, the presently preferred implementation places cysteines at the end of the peptide. These form a cyclic disulfide is conformation resembles that of the natural were turned in a natural protein. Again, the amino acids must have the D-configuration.

Figure 6:
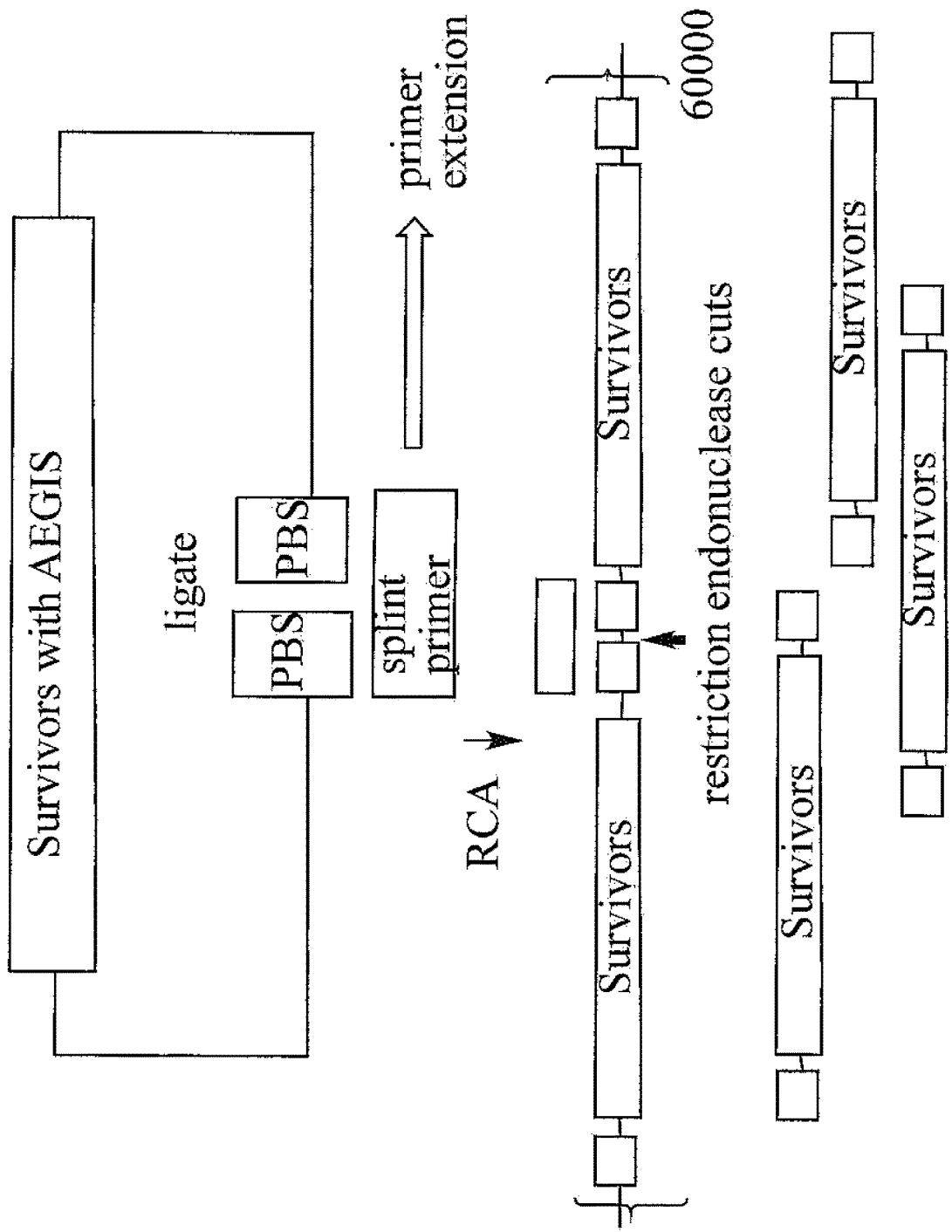
FIG. 6. Rolling circle amplification (RCA) is disclosing this diagram as an alternative to PCR way to amplify survivors from an AEGIS-LIVE, the process disclosed in the parents. Here, instead of the primer binding sites (PBS) being used to bind primers in the PCR, those same sites are used to anneal to a splint which allows the ligation of the survivors to form a circle. The splint can then be used as a primer for rolling circle amplification, leading to between 10,000 and 100.000 copies of the survivor sequence(s) as a linear concatamer. These can then be cleaved by a restriction enzyme placed strategically to yield the same number of short survivor sequence(s) which can be introduced into AEGIS-LIVE. The presently preferred polymerase for the RCA is Bst I or other polymerase disclosed in U.S. Pat. No. 90,602,345, also a descendent of U.S. patent application Ser. No. 12/999,138, which is incorporated herein by reference is entirely.

The process whereby PCR is replaced by rolling circle amplification (RCA) is disclosed in FIG. 6. The presently preferred polymerase for the RCA is Bst I or other polymerase disclosed in U.S. Pat. No. 90,602,345, also a descendent of U.S. patent application Ser. No. 12/999,138, which is incorporated herein by reference is entirely. Not disclosed in U.S. Pat. No. 90,602,345, and disclose here for the first time, is the use of the sequences that would be, in PCR amplification, the primer binding sites, instead to template the ligation to form a circle with a splint complement. That may, optionally, also be used as the primer for the RCA. Finally, after the concatamer is created, the short survivors can be generated by digestion by restriction endonuclease at a restriction site placed strategically in the primer binding sites. The short survivors can then be put into the next cycle of AEGIS-LIVE.

Further loss of isoguanosine (B) species can be mitigated by using 7-deazaisoguanosine in the RCA process, or by using thiothyrnidine in the process to suppress mispairing between thymidine and isoguanosine and isoguanosine analogs in the template. Both of these are in the most preferred embodiments in the structure shown in FIG. 1.

EXAMPLES

Example 1

Synthesis of a glycal Having the Unnatural L-configuration

Figure 3:
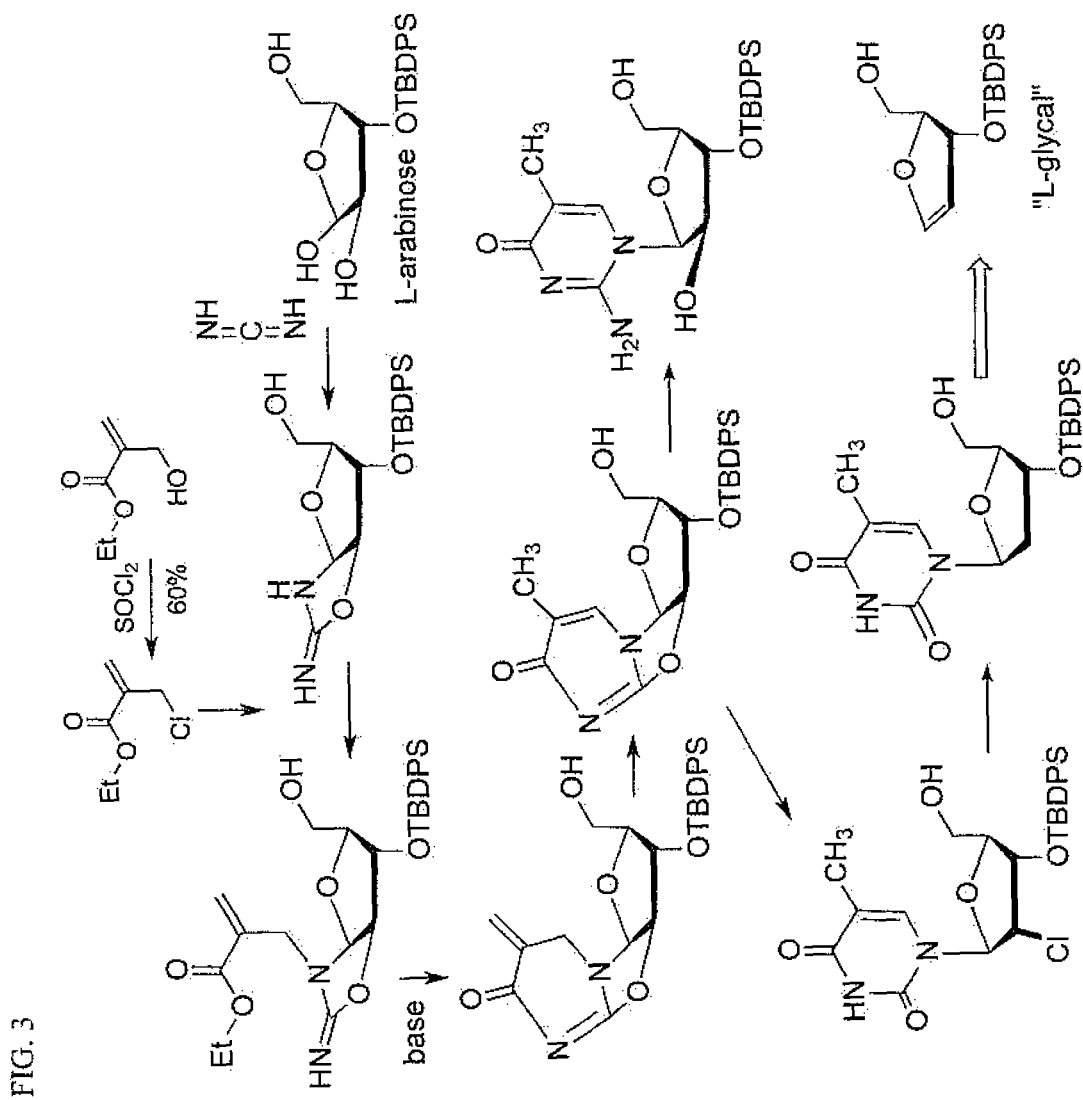
FIG. 3. Synthetic route generates a glycal having the L-configuration. This is a precursor for synthesizing all C-glycosides in the instant invention, specifically from FIG. 1, the heterocycles implementing the V, K. and Z hydrogen bonding patterns, and in FIG. 2, the heterocycles implementing the S, V, K, and Z hydrogen bonding patterns following routes covered in the parents of the instant application. This drawing also described the route to prepare the FIG. 1 AEGIS S in its epimeric form.

The mirror image L-nucleotides for G, A, T, and C needed to construct the L-AEGISbodies are commercially available. However, the L-AEGIS nucleotides that are used to synthesize the L-AEGISbodies are not. The precursor for the AEGIS components that are C-glycosides is prepared by the literature route shown in FIG. 3. Arabinose, a very inexpensive L-sugar, is the precursor. The same route, adapted from the parents for the L-glycal, leads to the formation of RNA AEGIS building blocks.

Example 2

Figure 2:
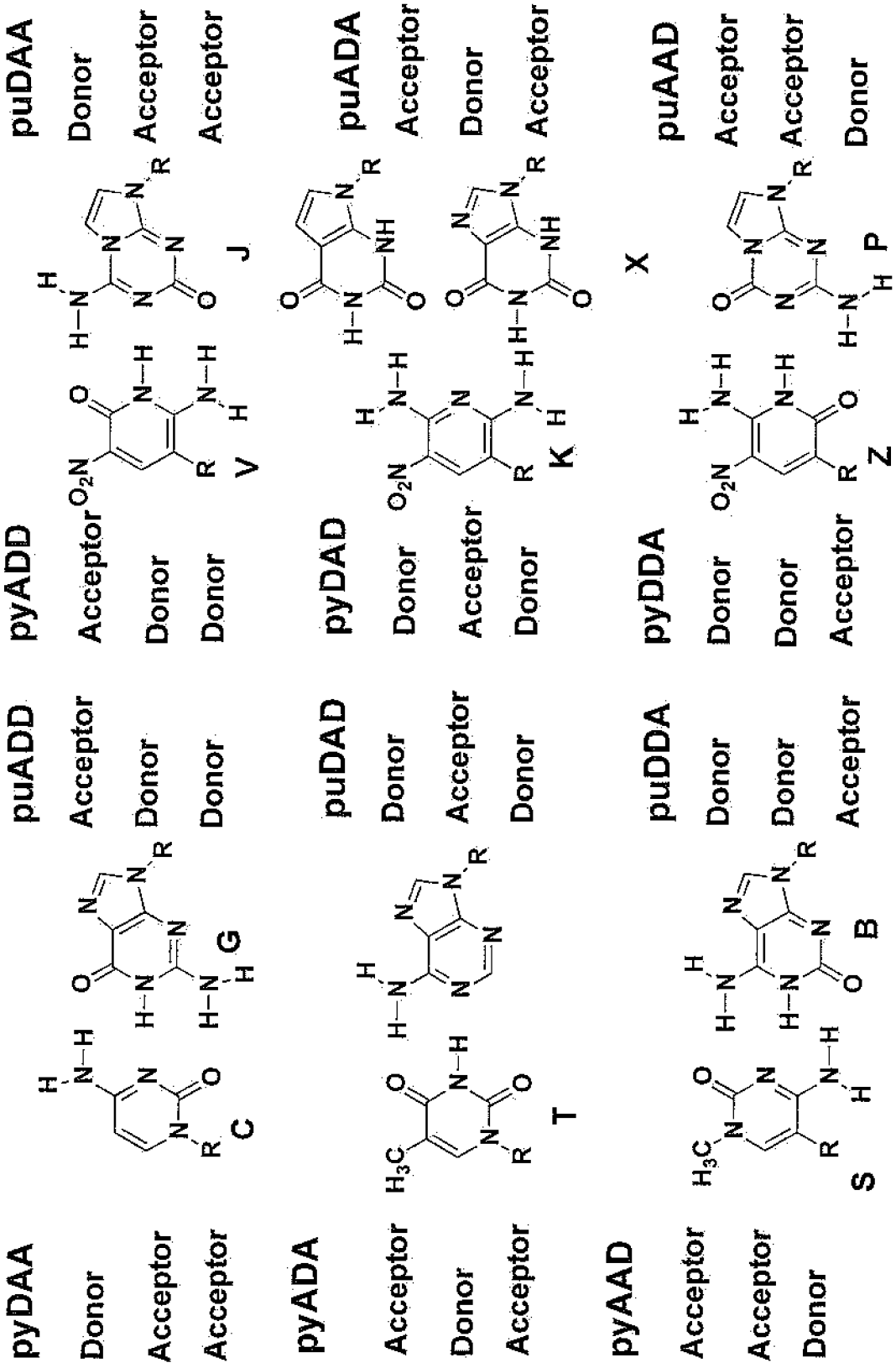
FIG. 2. This invention teaches the different heterocycles can implement the same hydrogen bonding pattern. Shown here are presently preferred heterocycles for implementing the instant invention, as alternatives. The nucleotides herein that are not found in natural DNA or RNA are called "non-standard".

Synthesis of a L-AEGIS nucleoside phosphoramidites Suitable for Solid Phase DNA Synthesis, Here Implementing the Z Hydrogen Bonding Pattern from FIG. 2

Figure 4:
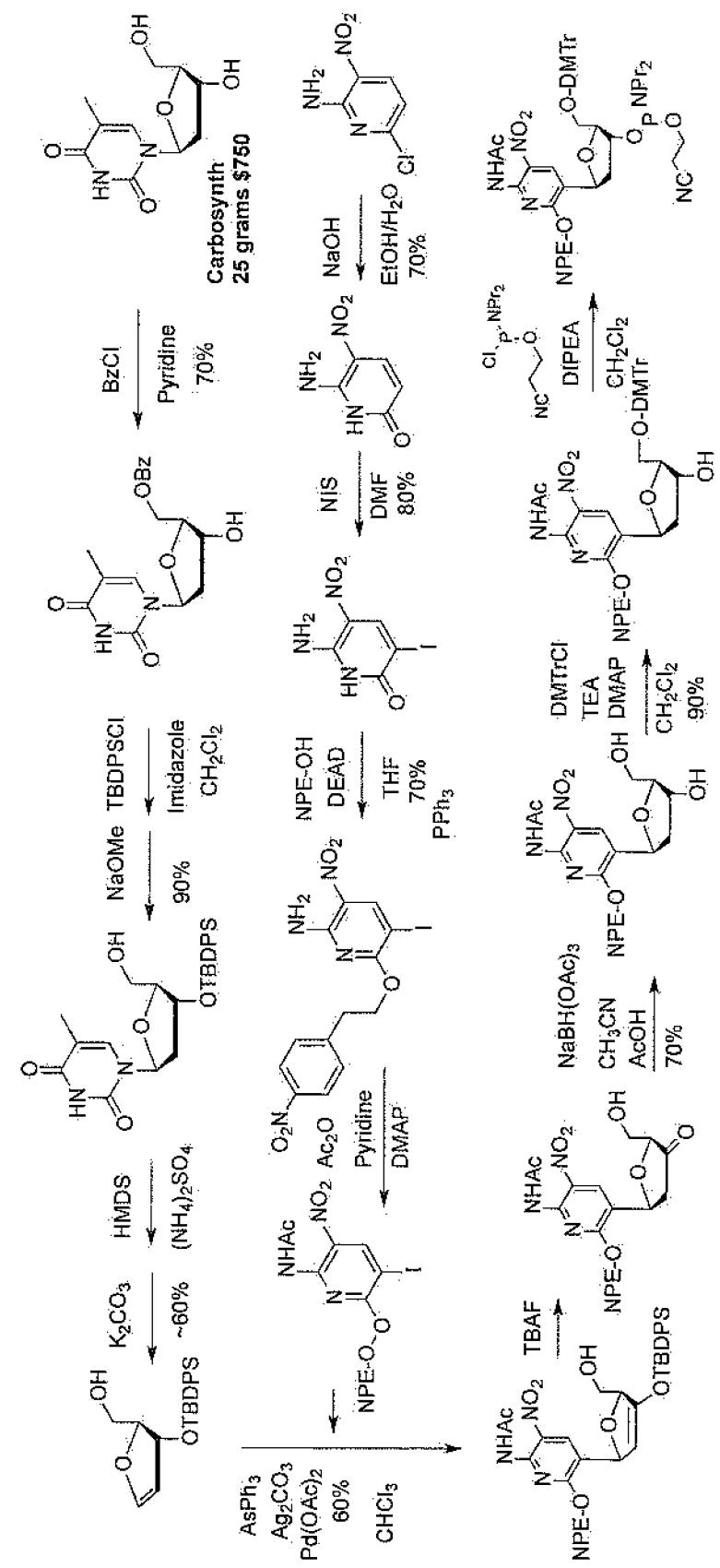
FIG. 4. Synthetic route to a protected phosphoramidite of AEGIS Z follows routes that are described in the parents. The precursor is commercially available from Carbosynth.
Figure 5:
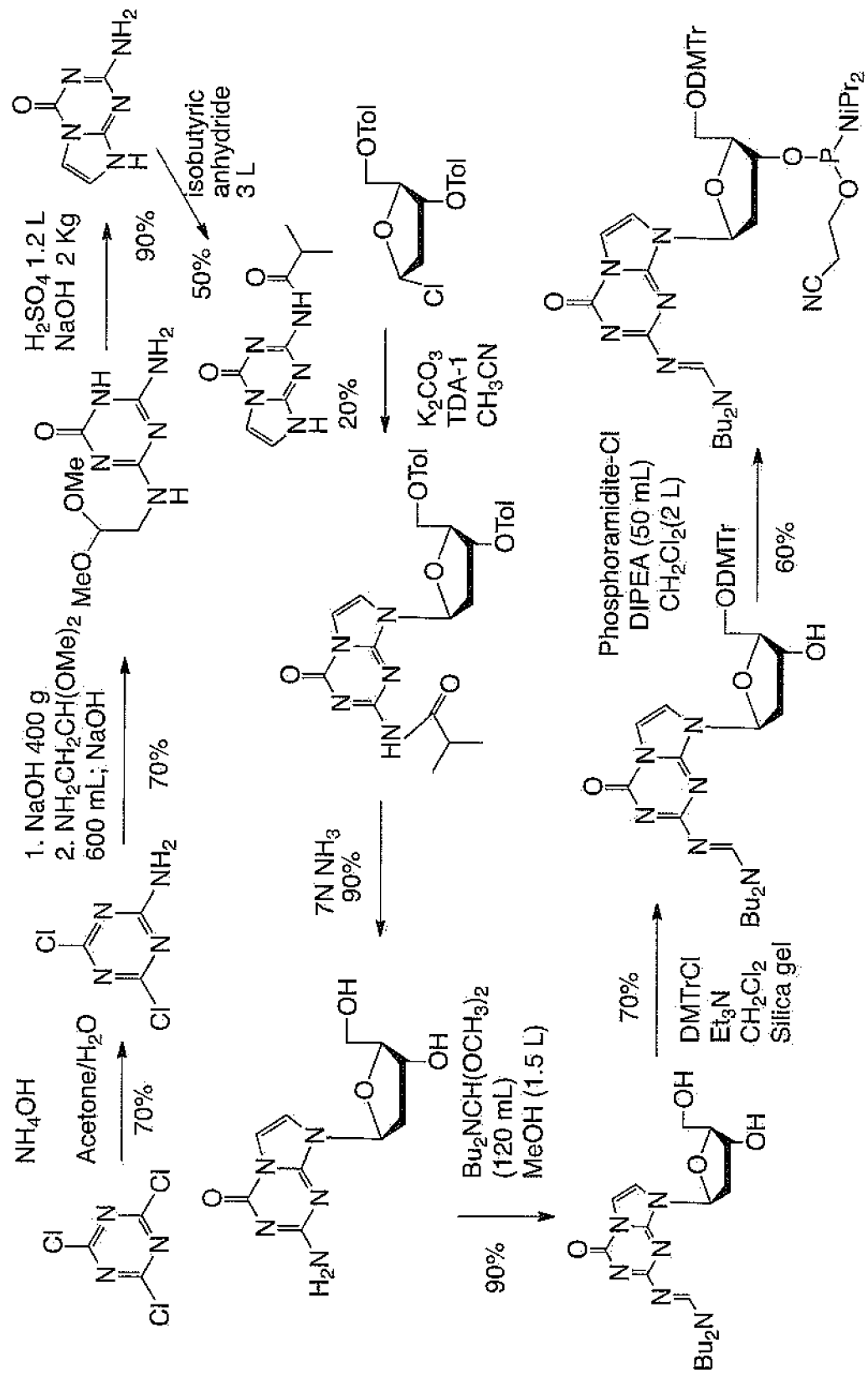
FIG. 5. Synthetic route to generate L-AEGIS P. Other AEGIS N-glycoside analogs are prepared analogously following routes described for the D-enantiomer in the parents.

An alternative route to C-glycosidic AEGIS components that are C-glycosides is shown in FIG. 4. This alternative route starts from L-thymidine, which is presently available from Carbosynth for $750/25 grams. This also follows synthetic procedures disclose in the parents. The inversion of configuration does not change any of the chemistry involved.

Example 3

Synthesis of a L-AEGIS Nucleoside Phosphoramidites Suitable for Solid Phase DNA Synthesis, Here Implementing the P Hydrogen Bonding Pattern from FIG. 1 and FIG. 2

The route to prepare N-glycosidic AEGIS components in a protected form. This starts with the-L chlorosugar. Again, this follows synthetic procedures disclose in the parents. The inversion of configuration does not change any of the chemistry involved.

What is claimed is:

1. A process for binding to a preselected target, said process comprising contacting said target with an oligonucleotide segment, wherein at least one nucleotide of said oligonucleotide has a nucleobase selected from the group consisting of

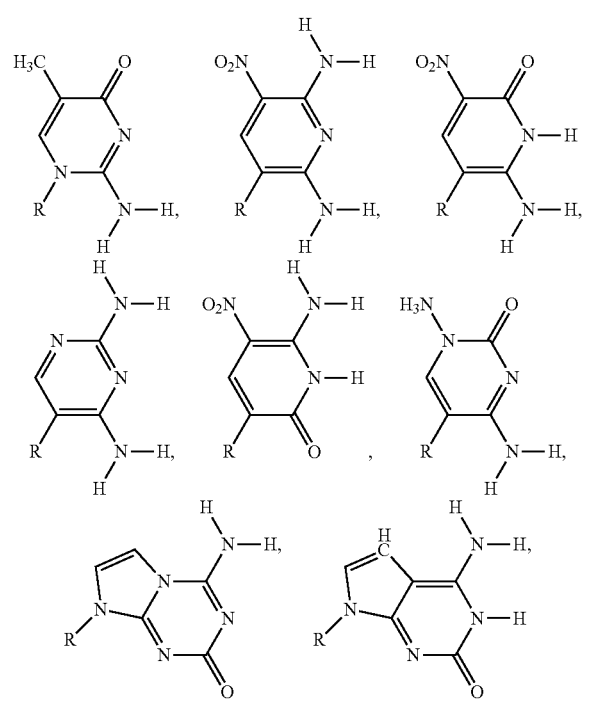

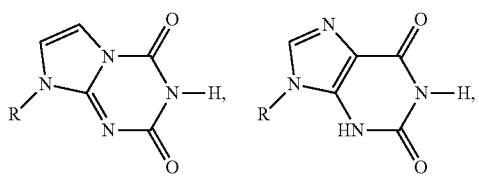

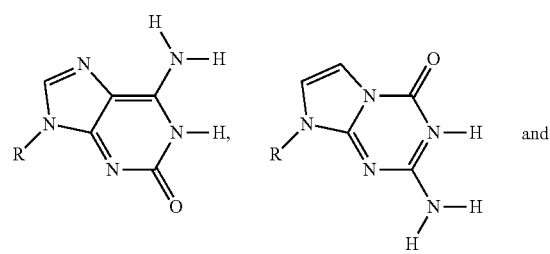

wherein R is the point of attachment of said nucleobase to said oligonucleotide, wherein said target is not Watson-Crick complementary to said oligonucleotide, and either wherein all of the carbohydrates of said oligonucleotide have D-configurations or all of the carbohydrates of said oligonucleotide have L-configurations.

2. The process of claim 1, wherein said nucleobase is

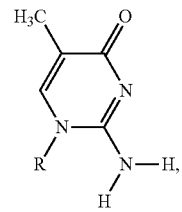

where R is the point of attachment of said nucleobase to said oligonucleotide.

3. The process of claim 1, wherein said nucleobase is

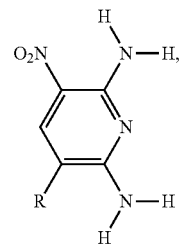

where R is the point of attachment of said nucleobase to said oligonucleotide.

4. The process of claim 1, wherein said nucleobase is

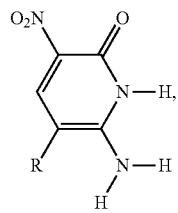

where R is the point of attachment of said nucleobase to said oligonucleotide.

5. The process of claim 1, wherein said nucleobase is

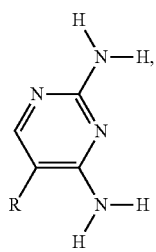

where R is the point of attachment of said nucleobase to said oligonucleotide.

6. The process of claim 1, wherein said nucleobase is

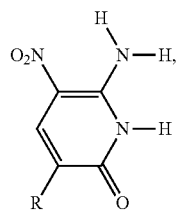

where R is the point of attachment of said nucleobase to said oligonucleotide.

7. The process of claim 1, wherein said nucleobase is

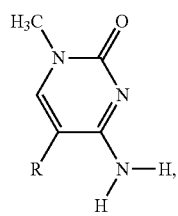

where R is the point of attachment of said nucleobase to said oligonucleotide.

8. The process of claim 1, wherein said nucleobase is

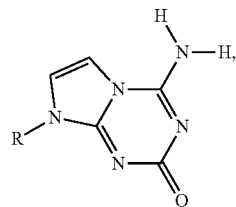

where R is the point of attachment of said nucleobase to said oligonucleotide.

9. The process of claim 1, wherein said nucleobase is

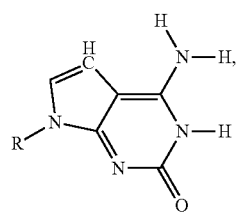

where R is the point of attachment of said nucleobase to said oligonucleotide.

10. The process of claim 1, wherein said nucleobase is

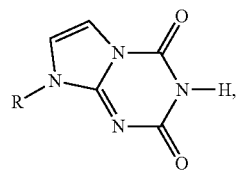

where R is the point of attachment of said nucleobase to said oligonucleotide.

11. The process of claim 1, wherein said nucleobase is

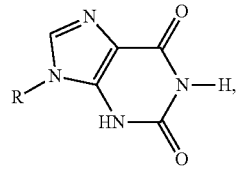

where R is the point of attachment of said nucleobase to said oligonucleotide.

12. The process of claim 1, wherein said nucleobase is

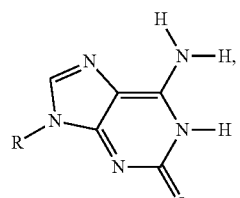

where R is the point of attachment of said nucleobase to said oligonucleotide.
13. The process of claim 1, wherein said nucleobase is
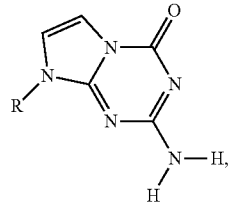
where R is the point of attachment of said nucleobase to said oligonucleotide.
14. The process of claim 1, wherein said nucleobase is
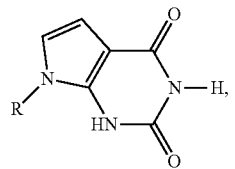
where R is the point of attachment of said nucleobase to said oligonucleotide.
* * * * *